United States Patent
Merritt (12)

(10) Patent No.: US 6,245,361 B1
(45) Date of Patent: *Jun. 12, 2001

(54) TUBERCULOCIDAL SYNERGISTIC DISINFECTANT COMPOSITIONS AND METHODS OF DISINFECTING

(75) Inventor: Colleen M. Merritt, Racine County, WI (US)

(73) Assignee: S. C. Johnson Commercial Markets, Inc., Sturtevant, WI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/909,131

(22) Filed: Aug. 11, 1997

Related U.S. Application Data

(62) Division of application No. 08/515,314, filed on Aug. 15, 1995, now abandoned.

(51) Int. Cl.[7] ............ A01N 33/12; A01N 43/64; A01N 43/66; A01N 59/08
(52) U.S. Cl. ............ 424/665; 424/661; 514/241; 514/242; 514/642; 514/643
(58) Field of Search ............ 424/665, 661; 514/642, 643, 241, 242

(56) References Cited

U.S. PATENT DOCUMENTS

| | | | |
|---|---|---|---|
| 2,987,435 | 6/1961 | Davies et al. | 167/18 |
| 3,201,311 | 8/1965 | Antonides et al. | 167/22 |
| 3,669,891 | 6/1972 | Greenwood et al. | 252/90 |
| 3,836,669 | 9/1974 | Dadekian | 424/329 |
| 3,852,210 | 12/1974 | Krezanoski | 252/95 |
| 4,005,028 | 1/1977 | Heckert et al. | 252/99 |
| 4,073,888 | 2/1978 | Snyder | 424/149 |
| 4,113,645 | 9/1978 | DeSimone | 252/187 |
| 4,169,065 | 9/1979 | Robertson | 252/95 |
| 4,264,466 | 4/1981 | Carleton et al. | 252/99 |
| 4,320,147 | 3/1982 | Schaeufele | 424/329 |
| 4,336,151 | 6/1982 | Like et al. | 252/106 |
| 4,418,055 | 11/1983 | Andersen et al. | 424/126 |
| 4,444,790 | 4/1984 | Green et al. | 424/329 |
| 4,461,652 | 7/1984 | Richmond | 134/2 |
| 4,464,398 | 8/1984 | Sheets et al. | 424/329 |
| 4,499,077 | 2/1985 | Stockel et al. | 424/149 |
| 4,540,505 | 9/1985 | Frazir | 252/106 |
| 4,576,728 | 3/1986 | Stoddart | 252/102 |
| 4,783,283 | 11/1988 | Stoddart | 254/547 |
| 4,797,221 | 1/1989 | Gueldenzopf | 252/95 |
| 5,080,826 | 1/1992 | Colborn et al. | 252/187.25 |

FOREIGN PATENT DOCUMENTS

| | | |
|---|---|---|
| 2180629 | 11/1972 | (FR) . |
| 1 282 118 | 2/1975 | (GB) . |
| 1466560 | 3/1977 | (GB) . |
| 1548379 | 7/1979 | (GB) . |

OTHER PUBLICATIONS

W. Rutala, et al., "Inactivation of *Mycobacterium tuberculosis* and *Mycobacterium bovis* by 14 Hospital Disinfectants," *American Journal of Medicine*, vol. 91(suppl 3B), pp. 3B–267S to 3B–271S (1991).

M. Best, et al., "Efficacies of Selected Disinfectants against *Mycobacterium tuberculosis*," *Journal of Clinical Microbiology*, vol. 28(10), pp. 2234–2239 (1990).

J. Dos Reis Meirelles Neto et al., "Tuberculocidal activity of some cationic detergents" ("Atividade tuberculocida de alguns detergentes cationicos"), *Folha Med.*, vol. 87(4), pp. 227–232 (1983).

L. Szymaczek–Meyer et al., "Effect of some disinfectants (Phenol derivatives, quaternary ammonium compounds, aldehydes and chloramine) on human type tubercle bacilli sensitive and resistant to antibacillary drugs," *Med. Dosw. Mikrobiol.*, vol. 31(1), pp. 53–59 (1979).—Full English Translation of Article—11 pages.

*Primary Examiner*—Allen J. Robinson
(74) *Attorney, Agent, or Firm*—Neil E. Hamilton; Warren R. Bovee; Renee J. Rymarz

(57) ABSTRACT

An aqueous cleaning and disinfecting composition is disclosed that is a synergistic combination of (a) a sufficient amount of a chlorine-containing bleach compound such as sodium hypochlorite or sodium dichloroisocyanurate to provide from about 1,100 parts per million by weight of available chlorine level with (b) from about 600 to 800 parts per million by weight of bactericidal quaternary ammonium compounds such as mixtures of didecyldimethylammonium chloride and ($C_{12}$–$C_{16}$ alkyl)dimethylbenzylammonium chlorides. Such compositions are tuberculocidal at unexpectedly low concentrations. Also disclosed are two component compositions and methods of disinfecting surfaces containing tubercle bacilli and other pathogenic microorganisms such as bacteria and viruses.

20 Claims, No Drawings

TUBERCULOCIDAL SYNERGISTIC DISINFECTANT COMPOSITIONS AND METHODS OF DISINFECTING

This application is a continuation of Ser. No. 08/515,314, filed Aug. 15, 1995, now abandoned.

TECHNICAL FIELD

This invention relates to aqueous cleaning and disinfecting compositions that contain a synergistic combination of specific amounts of a chlorine bleach compound with specific amounts of bactericidal quaternary ammonium compounds wherein the compositions are tuberculocidal at unexpectedly low concentrations as well as to methods of disinfecting surfaces containing tubercule bacilli and other pathogenic micro-organisms such as bacteria and viruses.

BACKGROUND ART

Complete elimination of pathogenic micro-organisms on various surfaces, especially hard surfaces where such organisms may stay active for relatively long periods of time, has long been a goal of those charged with cleaning and maintaining in an antiseptic fashion commercial and institutional settings such as hospitals, medical clinics, meat packing and food preparation areas. A variety of chemical disinfecting agents have been developed to accomplish that goal. However, some of these agents have disadvantages in that some are corrosive or unpleasant to smell or capable of staining certain surfaces that commonly need to be cleaned and disinfected. Furthermore, some such agents are simply not effective against certain of the micro-organisms that may be found in institutional settings.

Tubercle bacilli create a significant problem in commercial and institutional settings, especially in hospitals, because of their tendency to be rather easily transmitted from one person to another. A number of researchers have reported on the efficacy of various chemical disinfecting agents to eliminate tubercle bacilli.

An article by W. A. Rutala, et al. entitled "Inactivation of *Mycobacterium tuberculosis* and *Mycobacterium bovis* by 14 hospital disinfectants" (*American Journal of Medicine*, vol. 91(3B), pages 267S–271S (1991)) reports that chlorine dioxide, 0.80% hydrogen peroxide plus 0.06% peroxyacetic acid and an iodophor achieved complete inactivation of both of the titled micro-organisms while two different quaternary ammonium compounds as well as 100 parts per million ("ppm") of chlorine were not effective against both micro-organisms. They reported that glutaraldehydes, a phenolic and chlorine (1,000 ppm) were completely effective against *Mycobacterium tuberculosis* and showed good inactivation of *Mycobacterium bovis*. This article reports on page 268S that *Mycobacterium tuberculosis* "was studied because it is a recognized human pathogen that has been associated with infections caused by ineffective disinfectants or disinfection procedures . . . and [*Mycobacterium*] *bovis* was selected because it is the organism required by the AOAC for tuberculocidal activity testing . . . ."

An article by M. Best et al. entitled "Efficacies of selected disinfectants against *Mycobacterium tuberculosis*" (*Journal of Clinical Microbiology*, vol. 28(10), pages 2234–9 (1990)) likewise reported that the quaternary ammonium compound tested (0.04% dimethyl benzylammonium chloride) was ineffective against *Mycobacterium tuberculosis*. It also reported that sodium hypochlorite required a higher concentration (10,000 parts per million "ppm") of available chlorine to achieve an effective level of disinfection than did sodium dichloro isocyanurate (6,000 ppm).

Chlorine bleaches such as aqueous sodium hypochlorite have long been recognized as being effective against all types of micro-organisms provided that the bleach is used in sufficiently high concentrations such as 5,000 ppm (0.5%) of active sodium hypochlorite and higher depending on the micro-organism to be eliminated. These types of solutions are recommended for use for disinfecting an area where blood or other potentially pathogenic biological contaminants have been spilled or released and total disinfection is required. At such high levels of sodium hypochlorite, the chlorine smell from the bleach simply makes this agent undesirable for routine cleaning and disinfection of, for example, hospital rooms, where patients remain in the room during and after the cleaning and disinfection process.

A sterilization system based on a chlorine bleach disinfecting agent that uses two baths in which articles to be sterilized are placed is described in U.S. Pat. No. 4,418,055 to Andersen et al. In this system, the ingredients used in the sterilization system are stored in hermetically sealed bags that keep reactive ingredients away from each other until use. The bags also provide premeasured quantities of the ingredients to avoid any errors that might be caused by having the user measure out each component needed.

Quaternary ammonium compounds have long been recognized as being useful for their antibacterial properties as can be seen from U.S. Pat. No. 3,836,669 to Dadekian; U.S. Pat. No. 4,320,147 to Schaeufele; U.S. Pat. No. 4,336,151 to Like et al.; U.S. Pat. No. 4,444,790 to Green et al.; U.S. Pat. No. 4,464,398 to Sheets et al.; and U.S. Pat. No. 4,540,505 to Frazier.

Higher levels of quaternary ammonium compounds have been reported as being effective disinfectants against various pathogenic micro-organisms, even including *Mycobacterium tuberculosis*. J. Dos Reis Meirelles Neto et al. report in their article entitled "Tuberculocidal activity of some cationic detergents" ("Atividade tuberculocida de alguns detergentes cationicos")—*Folha Med.*, vol. 87(4), pages 227–232 (1983)—that the quaternary ammonium salts benzalkonium chloride, ammonium-alkyl-dimethylbenzyl chloride plus ammonium-alkyl-dimethylethyl-benzyl chloride and cetylpyridinium chloride in a concentration of 0.4% showed microbiocidal action to sputum microbial flora and some toxic effect to *Mycobacterium tuberculosis*.

Another article by L. Szymaczek-Meyer et al. entitled "Effect of some disinfectants (phenol derivatives, quaternary ammonium compounds, aldehydes and chloramine) on human type tubercle bacilli sensitive and resistant to antibacillary drugs" (*Med. Dosw. Mikrobiol*, vol. 31(1), pages 53–59 (1979)) reported the results of using commercial concentrations of available hospital disinfectants on dense suspensions of tubercle bacilli strain Hsub 3sub 7Rv and human type wild strains sensitive and resistant to antibacillary drugs. They found that some of the disinfectants checked were tuberculocidal, but generally used solutions containing at least about 0.6% active disinfecting agent.

To minimize expense, undesirable odors and possible detrimental effects of disinfecting agents on surfaces to be disinfected, it is desirable to minimize the amount of disinfecting agents used while still retaining efficacy against pathogenic micro-organisms, especially against tubercle bacilli such as *Mycobacterium tuberculosis*. As will be explained in greater detail below, I have found that a combination of a specific amount of a chlorine bleach compound such as sodium dichloro isocyanurate with a specific amount of a bactericidal quaternary ammonium compound provides a composition that is effective against tubercle bacilli even though the concentration of the each compound used, when evaluated individually at that concentration, is ineffective against tubercle bacilli.

In the past, combinations of chlorine or peroxygen bleaches with quaternary ammonium compounds have been taught, but for different purposes or at different use levels than I have discovered. Typically, a relatively large amount of chlorine bleach (0.5% to 1% or more of active bleach compound which is 5,000 to 10,000 ppm of active bleach compound) has been combined with cationic surfactants (which typically refer to quaternary ammonium compounds generally and not all of these compounds possess bactericidal or disinfectant properties). If a sufficiently high amount of bleach compound is used (i.e., that, by itself, is capable of destroying pathogenic micro-organisms, including tubercle bacilli), then there is no need to include a bactericidal quaternary ammonium compound for disinfection purposes.

U.S. Pat. No. 3,669,891 to Greenwood et al. teaches various compositions that emit visible light during use. Example 8 teaches a two-component air freshener/germicidal composition that comprises a combination of an aqueous sodium hypochlorite solution (0.5% available chlorine) and a second solution containing 1% cetyl trimethylammonium bromide and 1.5% oleyl di-betahydroxyethyl methylammonium methosulfate. The two solutions were combined in the nozzle of a two compartment pump spray package set to deliver equal quantities of liquid from each compartment. Thus, the level of all quaternary ammonium compounds alone in the mixed liquids was 0.75% or 7,500 ppm of active material.

U.S. Pat. No. 2,987,435 to Davies et al. teaches synergistically active germicidal materials and methods for cleaning and disinfecting materials by combining a hypochlorite with a quaternary ammonium compound. One such method involves contacting a surface with a composition containing sodium hypochlorite at an available chlorine level of 0.45% to 5%, followed by contacting the surface with an aqueous solution of benzalkonium chloride (0.05% to 5.0% by weight, preferably 0.02%). Another method involves applying a solution comprising about 0.45% to about 5% by weight of available chlorine and from about 0.5% to 5% of benzalkonium chloride. Davies et al. teaches that the active materials are added such that the composition contains the equivalent of at least 0.1% by weight of available chlorine and 0.01% by weight of quaternary ammonium salt. Preferably, the compositions contain from 0.1% to 5% by weight of available chlorine and from 0.05 to 20 parts of quaternary ammonium salt are incorporated for each part by weight of chlorine. Davies et al. teaches that a concentrated aqueous germicidal solution can be made that is a solution of aqueous sodium hypochlorite solution containing from 0.25% to 1.5% available chlorine to which is added from 2.5% to 7.5% of a quaternary ammonium salt to form a concentrate and thereafter the concentrate is diluted 40-fold to obtain a germicidal bleaching solution.

U.S. Pat. No. 3,852,210 to Krezanoski teaches a stable liquid detergent containing active oxygen for use as a bleaching and cleaning composition, particularly for the skin. It contains from 0.1% to 50% of detergent vehicle-soluble peroxygen compounds as the active ingredient and, optionally, from 0.01% to 10% of a quaternary ammonium surfactive agent. The latter are added for the purpose of increasing detergency and foam stability as well as for imparting residual germicidal activity. U.S. Pat. No. 4,169,065 to Robertson teaches an ear cleaning mixture for canines containing a mixture of alcohol, acetic acid, hydrogen peroxide (0.3% to 3%), (soap) benzethonium chloride (0.01% to 0.06%), and water. Neither of these patents suggest the use of chlorine bleaches.

Cleaning compositions which may contain bleach compounds plus organosilicon quaternary ammonium compounds (to provide residual antibacterial activity to surfaces cleaned with such compositions) are taught in U.S. Pat. No. 4,783,283 to Stoddart (alkali metal hypochlorite level of from 1% to 12%); U.S. Pat. No. 4,576,728 to Stoddart (alkali metal hypochlorite level of from 1% to 12%); and U.S. Pat. No. 4,005,028 to Heckert et al. (any chlorine yielding bleach wherein the available chlorine content of the cleaning composition ranges from 0.5% to 10%). These patents do not suggest the use of organic quaternary ammonium compounds that are free of silicon.

Stable perfumed or thickened chlorine bleach compositions which may contain quaternary ammonium compounds are known. U.S. Pat. Nos. 4,113,645 to DeSimone teaches aqueous household bleach compositions containing from 5% to 15% of sodium hypochlorite along with 0.025% to 1% (based on the weight of the aqueous bleach composition) of a quaternary ammonium salt where the latter is to help disperse a perfume oil within the bleach composition to mask the smell of the household bleach composition.

U.S. Pat. No. 5,080,826 to Colborn et al. teaches stable fragranced household bleach compositions in which an immiscible or slightly miscible fragrance is dispersed in the bleach without wetting the interior walls of the plastic bleach container. Colborn et al. teach that 0–100 ppm of various surfactants can be used to disperse the fragrance within the bleach composition, wherein such surfactants include quaternary ammonium compounds.

British Patent No. 1,466,560 to Jeyes Group Ltd. teaches thickened aqueous solutions of alkali metal hypochlorites (1% to 14% available chlorine) for use in cleaning and disinfecting various surfaces, especially vertical surfaces. A combination of an alkali metal sarcosinate surfactant with another surfactant that can include quaternary ammonium compounds are useful as the thickening agents. British Pat. No. 1,548,379 to Jeyes Group Ltd. is similar to the '560 Patent except it uses a thickening agent for aqueous solutions of alkali metal hypochlorites composed of a sucrose surfactant and one or more other surfactants that are soluble in the hypochlorite, including quaternary ammonium compounds.

U.S. Pat. No. 4,264,466 to Carleton et al. teaches mulls consisting of a liquid phase and a dispersed solid phase. The mulls can be used as detergents and may include water sensitive detergency adjuvants such as bleaches as well as cationic surfactants. Some of the cationics are said to be able to provide sanitization of the washload, but are primarily useful as suspension agents for the dispersed solids.

U.S. Pat. No. 4,461,652 to Richmond teaches process and product for removing barnacles from marine vessels that is composed of a stock mixture of (1) 15% to 35% hydrocarbon liquid; (2) 1.5% to 6% of surfactant that can include the alkyl, dialkylbenzylammonium salt of (5) below; (3) 0% to 2% alcohol; (4) 0.5% to 5% metal hypochlorite; (5) 0.5 to 1.5% alkyl, dialkylbenzylammonium salt; (6) 30% to 50% water; and 52.5% to 0.5% inert carriers. The stock mixture may be diluted substantially 1:1 with water prior to use.

SUMMARY DISCLOSURE OF THE INVENTION

One object of this invention is to provide disinfectant compositions that can be used in a method of disinfecting various surfaces to inactivate tubercle bacilli. Another object of this invention is to provide such compositions that can remain stable and effective for extended periods of time because the active ingredients are separated from each other until use.

A particularly advantageous object of this invention is to provide compositions that can be used in commercial and institutional settings for cleaning and disinfection purposes that are more tolerable to people remaining in the area disinfected because the smell of the compositions is much lower than if more highly concentrated hypochlorite bleach compositions were used as the active disinfectant. Yet another object is to provide cleaning and disinfectant compositions that are capable of inactivating tubercule bacilli, but do not have high concentrations of disinfectant compounds and are thus less prone to corrode or stain surfaces to be cleaned and disinfected.

These and other objects of the present invention are provided by a method of disinfecting a surface containing tubercule bacilli comprising applying to that surface an aqueous composition comprising, as disinfecting agents, an amount of a chlorine-containing bleach compound such as sodium hypochlorite or sodium dichloro isocyanurate effective to provide from about 1,100 to about 2,500, more preferably from about 1,100 to about 2,200, parts per million by weight of available chlorine level and from about 600 to about 800, more preferably from about 650 to about 700, parts per million by weight of a bactericidal organic quaternary ammonium compound such as a mixture of didecyldimethylammonium chloride and ($C_{12}$–$C_{16}$ alkyl) dimethylbenzylammonium chlorides.

This invention also relates to a composition for disinfecting a surface containing tubercule bacilli comprising an aqueous composition comprising, as disinfecting agents, an amount of a chlorine-containing bleach compound such as sodium hypochlorite or sodium dichloro isocyanurate effective to provide from about 1,100 to about 2,500 parts per million by weight of available chlorine level and from about 600 to about 800 parts per million by weight of a bactericidal organic quaternary ammonium compound.

BEST MODE FOR CARRYING OUT THE INVENTION

To obtain proper disinfection of surfaces containing tubercule bacilli, two compounds are required to be present in the aqueous disinfecting compositions of the present invention.

The first required ingredient is a chlorine-containing bleach compound of the type that is well known and of which many are commercially available. In aqueous media, such compounds are sufficiently water dispersible to provide active species based on chlorine that have a deleterious effect on pathogenic micro-organisms as well possessing the properties of being able to "bleach" by rendering materials they contact colorless or white.

Examples of such chlorine-containing bleach compounds are those which yield an effective amount of a hypochlorite species in aqueous solution which is sufficient to be useful in the compositions of the present invention. The determination of which such compounds are useful in the present invention may readily be determined by dissolving the compound in water and measuring the active chlorine level of the aqueous solution. Such compounds may include alkali metal hypochlorites, alkaline earth metal hypochlorites, hypochlorite addition compounds, chloramines, chlorimines, chloramides, chlorimides and mixtures thereof. Specific examples of such compounds include sodium hypochlorite, potassium hypochlorite, monobasic calcium hypochlorite, dibasic magnesium hypochlorite, chlorinated trisodium phosphate dodecahydrate, trichlorocyanuric acid, 1,3dichloro-5,5-dimethylhydantoin, N-chlorosulfamide, chloramine T (sodium paratoluenesulfonchloramide available from R. W. Greeff & Company of Greenwich, Conn.), dichloramine T (N,N-dichloro-p-toluenesulfonamide), chloramine B (sodium benzenesulfochloramide) and dichloramine B. Presently preferred bleach compounds are alkali metal hypochlorites and alkali metal dichloroisocyanurates. The most preferred of those compounds are sodium hypochlorite and sodium dichloro isocyanurate since commercial quantities of such compounds are readily available.

The bleach compounds are present in amounts that are effective to provide from about 1,100 to about 2,500 parts per million by weight of available chlorine level based on the total weight of the composition with from about 1,100 to about 2,200 ppm being more preferred. Less than about 1,100 ppm of available chlorine level of bleach compound results in compositions which are not completely effective against tubercule bacilli and more than about 2,500 ppm of available chlorine level of bleach compound tends to provide disinfectant compositions that have strong odors of chlorine and hypochlorite as well as being more corrosive to surfaces being disinfected. The "available chlorine level" can be determined by well known methods such as iodometrically by titrating the aqueous solution containing active chlorine with sodium thiosulfate to obtain the concentration of available chlorine as sodium hypochlorite using well known analytical methods.

The organic quaternary ammonium compounds useful in the present invention are those that have bactericidal properties and that are relatively soluble in aqueous media. These compounds are also well known as can be seen from U.S. Pat. No. 3,836,669 to Dadekian; U.S. Pat. No. 4,320,147 to Schaeufele; U.S. Pat. No. 4,336,151 to Like et al.; U.S. Pat. No. 4,444,790 to Green et al.; U.S. Pat. No. 4,464,398 to Sheets et al.; and U.S. Pat. No. 4,540,505 to Frazier noted above. Many are commercially available materials sold under the tradenames of Bardac®, Barquat® and Hyamine® by Lonza, Inc. of Fairlawn, N.J., BTC by Stepan Company of Northfield Ill. and Maquat® by Mason Chemical Company of Arlington Heights, Ill.

Examples of such compounds are di($C_8$–$C_{12}$ alkyl)di ($C_1$–$C_4$ alkyl)ammonium salts where the salts include halides, sulfates, and methosulfates such as dioctyldimethyl ammonium chloride, didecyldimethylammonium chloride, didodecyldimethylammonium chloride, didecyldimethylammonium bromide, didecyldimethylammonium sulfate, didecyldimethylammonium methosulfate, or dioctyldiethyl ammonium chloride; ($C_{12}$–$C_{18}$ alkyl)di($C_1$–$C_4$ alkyl) benzylammonium salts where the salts include halides, sulfates, and methosulfates such as ($C_{12}$–$C_{16}$ alkyl) dimethylbenzylammonium chloride, bromide, sulfate or methosulfate; and (alkyl)di($C_1$–$C_4$ alkyl) ethylbenzylammonium salts where the salts include halides, sulfates and methosulfates such as ($C_{12}$–$C_{16}$ alkyl)dimethyl ethylbenzylammonium chloride, bromide, sulfate or methosulfate, and mixtures thereof. As is well known, the manufacturing processes used to prepare such compounds often result in mixtures of varying alkyl chain length compounds and thus the designation "$C_2$–$C_{18}$" is used to describe such compounds. Presently, the preferred quaternary ammonium compounds are a blend of didecyldimethylammonium chloride and ($C_{12}$–$C_{16}$ alkyl) dimethylbenzylammonium chloride, more preferably in a 51.5:48.5 ratio by weight.

The quaternary ammonium compounds are present in the composition in amounts ranging from about 600 to about 800 parts per million by weight of the total composition with from about 650 to about 700 ppm being more preferred. Less than about 600 ppm of quaternary ammonium compound results in compositions which are not completely effective against tubercule bacilli and more than about 800 ppm of quaternary ammonium compound tends to be wasteful and introduces more risk that the quaternary ammonium compound will stain surfaces being disinfected.

The above compounds are dissolved in water to form the disinfecting compositions of the present invention. As is generally used for conventional cleaning and disinfecting compositions, small amounts, generally less than about 5% by weight of the total composition, of various water miscible or soluble solvents such as lower alcohols such as ethanol and isopropanol, glycol ethers and the like may also be included to improve the cleaning efficiency or surface wetting ability of the compositions of the present invention.

The compositions of the present invention may also contain various conventional surfactants or detergents to assist in the cleaning and surface wetting properties of the disinfecting compositions provided that the surfactants or detergents are compatible with the bleach and quaternary ammonium compounds. Generally, the amounts of such surfactants or detergents does not exceed about 15% by weight of the total weight of the composition. Such surfactants or detergents include nonionic, amphoteric, zwitterionic and cationic surfactants. Generally, anionic surfactants tend to react with cationic materials such as the quaternary ammonium compounds and if any anionic surfactants are to be included, they should not interfere with the tuberculocidal disinfecting properties of the quaternary ammonium compounds to any significant degree. Nonionic surfactants such as alkyl amine oxides are presently preferred if such surfactants or detergents are to be included in the compositions of the present invention.

Builder salts and chelating agents of the type conventionally used in liquid detergent compositions for cleaning hard surfaces may also be included in the compositions of the present invention in small amounts, generally less than about 5%, provided that they do not interfere with the disinfecting properties of the composition. Such builder salts include sodium sesquicarbonate, sodium carbonate, sodium borate, potassium carbonate, tetrapotassium pyrophosphate, sodium metasilicate and the like. The chelating agents may include water soluble chelating agents such as alkali metal or substituted ammonium amino polycarboxylates such as sodium or potassium salts of ethylenediamine tetraacetic acid ("EDTA") such as tetrasodium EDTA.

Other conventional additives which do not interfere with the disinfecting properties of the compositions and are compatible with the other ingredients present in the composition may be included in minor amounts of no more than about 5% by weight of the total composition such as dyes, perfumes, and ultraviolet light stabilizers.

INDUSTRIAL APPLICABILITY

The compositions of the present invention are simple to produce and use. Since the bleach compound may tend to lose some of its ability to provide active chlorine species to eliminate the tubercule bacilli which is known to be difficult to inactivate. Thus, it is more preferred to separate the bleach compound from the quaternary ammonium compound until such time as the composition is to be used.

In one embodiment, all of the ingredients to be used in the composition may be mixed together with the exception of the bleach compound to form one component. The bleach compound may take the form of an aqueous solution of, for example, sodium hypochlorite, as a second component having sufficient sodium hypochlorite level to provide the desired available chlorine level when the first component is mixed with a preselected amount of the aqueous solution of sodium hypochlorite (second component).

Mixing of these two components can be done just prior to application to a surface containing tubercule bacilli can be done in several ways. U.S. Pat. No. 4,418,055 to Andersen et al. noted above provides one way by which this can be done simply by sealing correct quantities of each of the two components in separate bags which are then opened and mixed together shortly prior to application. Other possible ways are to place the disinfectant compositions to be separated, particularly where the bleach compound and other ingredients are solid, in separate sheets which are dissolvable in water such as those described in U.S. Pat. No. 4,797,221 to Gueldenzopf and are simply dropped into a container of water and allowed to dissolve until the contents are well mixed, thereby generating the disinfectant compositions of the present invention.

U.S. Pat. No. 3,669,891 to Greenwood et al. describes another way by which two components could be mixed which is by placing each component into a two compartment trigger sprayer bottle. When the trigger is depressed, preselected portions of each component are drawn into the spray head, mixed together and atomized onto the surface to be cleaned and disinfected.

In a less preferred embodiment, all ingredients may be mixed together and the resulting disinfecting composition can be stored until use. The available chlorine level of the stored disinfecting composition should be monitored to insure that a sufficient level of available chlorine is present before use in disinfecting surfaces containing tubercule bacilli.

Thus, the compositions can be applied to surfaces to be disinfected in a variety of ways such as by sponging, spraying, mopping, wiping, foaming, dipping and in various other ways that are commonly used for conventional disinfecting agents.

As noted in the Rutala et al. journal article noted above, compositions which are tuberculocidal tend to be very effective in disinfecting and inactivating lipophilic and hydrophilic viruses, yeasts, fungi and bacteria. Thus the compositions of the present invention will find use as multipurpose disinfectants for many surfaces needing disinfection such as countertops, work areas, rest rooms, meat packing rooms, food handling areas and the like.

The following Examples are provided to show various aspects of the present invention without departing from the scope and spirit of the invention. Unless otherwise indicated, all parts and percentages used in the following Examples are by weight. "Room temperature" is about 20° C. Milliliters are expressed as "ml", liters are "l", grams are "g" and millimeters are "mm".

In the following Examples, the effectiveness of various compositions against tubercule bacilli was evaluated by an independent laboratory using industry standard methods with certain modifications.

In the Examples, one series of the evaluations was conducted according to the *Official Methods of Analysis of the AOAC*, Fourteenth Edition, 1984, Chapter 4—Disinfectants, paragraphs 4.039–4.041. "Confirmative In Vitro Test for Determining Tuberculocidal Activity" with the following three modifications to adapt the procedure to the independent laboratory's facilities using *Mycobacterium Bovis*

(BCG) ATCC 35743 which was exposed to each solution for a period of ten minutes at 20° C. followed by an incubation period of 90 days at 37° C. ("TB TEST 1"):

Modification (1) The subculture used for each test was not shaken during the incubation period.

Modification (2) Glass culture tubes were of a smaller size than specified in the method. The volume of media added to those smaller tubes was also reduced. This smaller size was selected based on the availability of disposable glassware. Disposable glassware was used to avoid potential problems with residue accumulation in the glassware. Middlebrook 7H9 Broth Difco B and Kirchners Medium were added in 13.5 ml volumes to 16×150 mm tubes instead of 18 ml added to 25 mm diameter tubes. The amount of Middlebrook ADC Enrichment added to each tube was 1.5 ml instead of 2.0 ml.

Modification (3) To establish efficacy in the presence of an organic soil load, the method was modified to include a 5% organic soil load. This was incorporated in the method by adding 1 ml of sterile horse blood serum to 19 ml of the test organism culture used for soaking the carriers. Quantitative determinations of the microbial concentration on untreated control carriers both before and after drying were made.

In some of the Examples herein, the effectiveness of various compositions against tubercule bacilli was evaluated by an independent laboratory using a second method that followed the method described in the *Official Methods of Analysis of the AOAC*, Fifteenth Edition, 1990, Chapter 6—Disinfectants, Section 965.12D–F. "Confirmative In Vitro Test for Determining Tuberculocidal Activity" using *Mycobacterium Bovis* (BCG) from Bionetics Research, Inc. (AKZO Teknika Corporation) which was exposed to each solution for a period of ten minutes at 20° C. followed by an incubation period of 60 days at 37° C. using the same Modifications (1), (2) and (3) to TEST METHOD 1, above ("TB TEST 2").

Some of the Examples used a modification of TB TEST 2 wherein the only modifications of the published method used were Modifications (1) and (2) to TEST METHOD 1, above ("TB TEST 3").

Some of the Examples used a modification of TB TEST 2 wherein the only modifications of the published method used were Modifications (1) and (3) to TEST METHOD 1, above ("TB TEST 4").

In the following Examples, the available chlorine level was determined just before the AOAC Confirmative Tuberculocidal Tests were conducted. That determination was made using the iodometric method for the evaluation of NaOCl (titration of available chlorine using aqueous sodium thiosulfate to an iodine endpoint) using Iodometric Method I described in Section 408A of the 16th Edition of *Standard Methods For the Examination of Water and Wastewater*, American Public Health Association, 1985 ("IODOMETRIC TITRATION METHOD"). The available chlorine as sodium hypochlorite in parts per million of the solution was obtained by multiplying the milliliters of sodium thiosulfate used in the titration of the sample by 35.46 (available chlorine factor) and dividing that by the amount in grams of sample used.

The following ingredients were used in the compositions described in the Examples:

Ammonium Hydroxide (28%)—ammonium hydroxide solution at 28% ammonia concentration.

Benzalkonium Chloride (50%)—solution of n-alkyl dimethyl benzylammonium chloride at 50% active concentration—Barquat® MB-50 from Lonza, Inc.

Citric Acid (50%)—aqueous solution of citric acid at 50% active concentration.

Caustic Soda (50%)—aqueous solution of sodium hydroxide at 50% active concentration.

Cocamide DEA—mixture of ethanolamides of coconut acid (Clindrol® CGN from Clintwood Chemical Company of Chicago, Ill.).

Didecyldimonium Chloride (50%)—solution of didecyl dimethylammonium chloride at 50% active concentration.

Didecyldimonium Chloride (80%)—solution of didecyl dimethylammonium chloride at 80% active concentration—Bardac® 22 from Lonza, Inc.

Hydroxyethylcellulose—Natrosol® 250H from Aqualon of Wilmington, Del.

KATHON® LX (14%)—5-chloro-2-methyl-4-isothiazolin-3-one from Rohm and Haas Company of Philadelphia, Pa. at 14% active concentration.

LAUNDRY BLEACH—standard household laundry bleach: Clorox® Bleach from The Clorox Company of Oakland, Calif. containing about 5.25% active chlorine level.

Lauramine Oxide (30%)—solution of lauryl dimethylammonium chloride at 30% active concentration.

Myristalkonium Chloride and Quaternium 14 (50%)—myristyldimethylbenzylammonium chloride and dodecyl dimethylethylbenzylammonium chloride at 50% actives concentration (BTC® 2125 from Stepan Company of Northfield, Ill.

Nonoxynol-9—polyoxyethylene (9.5) nonyl phenyl ether.

Octoxynol-9—polyoxyethylene (9) octyl phenyl ether (Triton® X-100 CG from Union Carbide Corporation of Danbury, Conn.).

Octoxynol-13—polyethylene glycol (13) octyl phenyl ether—Igepal® CO-720 from GAF Chemicals Corporation of Wayne, N.J.

Pareth 15-9—polyethylene glycol ether of a mixture of synthetic $C_{11}$–$C_{15}$ fatty alcohols with an average of 9 moles of ethylene oxide—Tergitol® 15-S-9 from Union Carbide Corporation of Danbury, Conn.

Polyquaternium 10—polymeric quaternary ammonium salt of hydroxyethylcellulose treated with a trimethylammonium substituted epoxide (Ucare® Polymer JR-400 from Amerchol Corporation of Edison, N.J.

SDI TABLET—3.5 g effervescent sodium dichloro isocyanurate tablet sold under the tradename CDB Sani Fizz 50LT by Olin Corporation of Chesire, Conn. (U.S. EPA Reg. No. 1258–1160). One such tablet was found to provide about 275 ppm of active chlorine level when dissolved in one gallon (3.79 l) of water.

Sodium Silicate (50%)—filtered aqueous sodium silicate solution at 50% active concentration.

Sodium Metasilicate—sodium metasilicate pentahydrate

Sodium Tripolyphosphate—anhydrous sodium tripolyphosphate.

T-EDTA (40%)—aqueous solution of tetrasodium salt of ethylenediamine tetraacetic acid at 40% active concentration.

TK-EDTA (50%)—tripotassium salt of ethylenediamine tetraacetic acid at 50% active concentration.

TKPP—Tetrapotassium Pyrophosphate, anhydrous.

It is quite common to provide cleaning and disinfecting compositions in concentrated forms that are intended to be diluted at the time of use. In the Examples, the following concentrated compositions were diluted with water just prior to evaluation:

CONC. A: To sufficient deionized water to obtain 100 parts by weight of concentrate are added with stirring 0.005 parts dye, 4 parts T-EDTA (40%); 1 part sodium sesquicarbonate; 4 parts Lauramine Oxide (30%); 0.3 parts fragrance; 10.88 parts Didecyldimonium Chloride (80%); and 16.38 parts Benzalkonium Chloride (50%).

CONC. B: 1.5 parts Octoxynol-13 and 1 part fragrance are mixed together to form a premix. The following ingredients are then blended together with 83.721 parts deionized water: 2.5 parts Citric Acid (50%); 1.25 parts sodium citrate; 10 parts Nonoxynol-9; 0.004 parts KATHONG® LX (14%); and 0.025 parts of dyes. The premix is then mixed into the blend with stirring. One batch of CONC. B was found to have a pH value of about 4.11.

CONC. C: 1.5 parts Octoxynol-13 and 1 part fragrance are mixed together to form a premix. The following ingredients are then blended together with 86.96 parts deionized water: 0.5 parts citric acid; 10 parts Nonoxynol-9; and 0.004 parts KATHON® LX (14%). The premix is then mixed into the blend with stirring. One batch of CONC. C was found to be a clear solution with a slight have having a pH value of 2.50.

CONC. D: To sufficient deionized water to obtain 100 parts by weight of concentrate are added with stirring 0.5 parts of a 1% solution of dye, 4 parts T-EDTA (40%); 1 part sodium sesquicarbonate; 4 parts Lauramine Oxide (30%); 0.3 parts fragrance; 10.88 parts Didecyldimonium Chloride (80%); and 16.38 parts Benzalkonium Chloride (50%).

CONC. E: The following were mixed with stirring in the order given and then allowed to stir for one to two hours until the solution became clear: 63.5 parts tap water; 9 parts T-EDTA; 8.75 parts Benzalkonium Chloride (50%); 8.75 parts Didecyldimonium Chloride (50%); 7 parts Pareth 15-9; and 3 parts sodium sesquicarbonate.

CONC. F: A small amount of deionized water was mixed with 0.005 parts of two dyes to form a slurry. Taking the amount of water used to form the slurry into consideration, a sufficient amount of water to form a total of 100 parts by weight of concentrate was charged into a mixing tank. The slurry was then added with stirring to the mixing tank. Thereafter, the following ingredients were added to the mixing tank in the order given: 1.8 parts Caustic Soda (50%); 4.0 parts Sodium Silicate (50%); 1.5 parts TK-EDTA (50%); 3.2 parts Sodium Tripolyphosphate; 3.2 parts Nonoxynol-9; 3.2 parts of Benzalkonium Chloride (50%); and 0.05 parts perfume.

CONC. G: This concentrate was produced by blending the following ingredients: 1872.28 parts deionized water; 1.50 parts Hydroxyethylcellulose; 2.00 parts Polyquaternium 10; 45.00 parts dipropylene glycol monomethyl ether; 4.62 parts Sodium Metasilicate; 32.02 parts TKPP; 18.98 parts Octoxynol-9; 2.00 parts Cocamide DEA; 3.80 parts fragrance; 8.54 parts Myristalkonium Chloride and Quaternium 14 (50%); and 9.26 parts Ammonium Hydroxide (28%).

1:128 CONC. D: 7.8 ml of CONC. A was mixed with sufficient AOAC HARD WATER to make 1,000 ml of solution.

1:256 CONC. D: 1.95 ml of CONC. D was mixed with sufficient AOAC HARD WATER to make 500 ml of solution.

1:100 CONC. E: 2.5 ml of CONC. E was mixed with sufficient sterile purified water to make 250 ml of solution.

1:10 CONC. F: 2.5 ml of CONC. F was mixed with sufficient AOAC HARD WATER to make 250 ml of solution.

1:10 LAUNDRY BLEACH—20 ml of LAUNDRY BLEACH was mixed with sufficient sterile purified water to make 200 ml of solution.

1:20 LAUNDRY BLEACH—10 ml of LAUNDRY BLEACH was mixed with sufficient sterile purified water to make 200 ml of solution.

1:35 LAUNDRY BLEACH—5.71 ml of LAUNDRY BLEACH was mixed with sufficient sterile purified water to make 200 ml of solution.

1:45 LAUNDRY BLEACH—4.44 ml of LAUNDRY BLEACH was mixed with sufficient sterile purified water to make 200 ml of solution.

To evaluate the efficacy of the compositions against tubercule bacilli under common conditions of use that normally involve the use of tap water that contains some degree of dissolved minerals as a diluent for concentrates, the concentrated compositions used in the Examples were diluted with AOAC Synthetic Hard Water containing 400 ppm $CaCO_3$ ("AOAC HARD WATER").

EXAMPLES 1–6

These Examples illustrate various application and comparative compositions which were evaluated for efficacy against tubercule bacilli. Various disinfectant compositions were evaluated, some of which further contained surfactants, other cleaning agents and additives in addition to quaternary ammonium compounds and compounds that provided active chlorine.

In some of these and the following Examples, a concentrate was diluted on a volume to volume basis with AOAC HARD WATER and, if applicable, a bleach compound providing active chlorine was then added. In other Examples, a bleach compound mixed with AOAC HARD WATER to obtain a disinfectant composition.

Table I lists the calculated total levels of both quaternary ammonium compounds and the active chlorine level for each diluted disinfectant composition. The results of evaluating the diluted disinfectant compositions by way of TB TEST 1, TB TEST 2 and TB TEST 3 are reported in Table I.

The diluted disinfectant composition of comparative Example 1A was prepared by mixing 2 ounces (59.1 ml) of CONC. A with sufficient AOAC HARD WATER to obtain 1 gallon (3.79 1) of composition.

Comparative Example 1B was prepared in the same manner as Example 1A, except 4 ounces (118 ml) of CONC. A was used.

Comparative Example 2A was prepared by mixing 0.5 ounces (14.8 ml) of CONC. B with sufficient AOAC HARD WATER to obtain 1 gallon (3.79l) of composition. Then, four SDI TABLETS were added to that composition and allowed to thoroughly disperse.

Comparative Example 2B was prepared in the same manner as Example 2A, except eight SDI TABLETS were added.

Comparative Example 3 was prepared by dissolving a sufficient number of SDI TABLETS in AOAC HARD WATER to obtain an active chlorine level of 5106.2 ppm.

Comparative Example 4 was prepared by mixing one part of LAUNDRY BLEACH with AOAC HARD WATER in a 1:10 volume:volume ratio to obtain an active chlorine level of 5106.2 ppm.

Comparative Example 5A was prepared by mixing 2 ounces (59.1 ml) of CONC. A with sufficient AOAC HARD WATER to obtain 4 gallons (15.1 l) of composition. Then one SDI TABLET was added to the resulting composition and allowed to thoroughly disperse.

Comparative Example 5B was prepared by mixing 1 ounce (29.6 ml) of CONC. A with sufficient AOAC HARD WATER to obtain 2 gallons (7.6 l) of composition. Then one SDI TABLET was added to the resulting composition and allowed to thoroughly disperse.

Comparative Example 5C was prepared by mixing 0.5 ounces (14.8 ml) of CONC. A with sufficient AOAC HARD WATER to obtain 1 gallon (3.79 l) of composition. Then one SDI TABLET was added to the resulting composition and allowed to thoroughly disperse.

Application Example 5D was prepared by mixing 0.5 ounces (14.8 ml) of CONC. A with sufficient AOAC HARD WATER to obtain 1 gallon (3.79 l) of composition. Then four SDI TABLETS were added to the resulting composition and allowed to thoroughly disperse.

Application Example 5E was prepared by diluting 0.5 ounces (14.8 ml) of CONC. A with sufficient AOAC HARD WATER to obtain 1 gallon (3.79 l) of composition. Then eight SDI TABLETS were added to the resulting composition and allowed to thoroughly disperse.

Comparative Example 6A was prepared by diluting 8 ounces (237 ml) of CONC. C with sufficient AOAC HARD WATER to obtain 4 gallons (15.1 l) of composition. Then one SDI TABLET was added to the resulting composition and allowed to thoroughly disperse.

Comparative Example 6B was prepared by diluting 4 ounces (118 ml) of CONC. C with sufficient AOAC HARD WATER to obtain 2 gallons (7.6 l) of composition. Then one SDI TABLET was added to the resulting composition and allowed to thoroughly disperse.

Comparative Example 6C was prepared by diluting 2 ounces (59.1 ml) of CONC. C with sufficient AOAC HARD WATER to obtain 1 gallon (3.79 l) of composition. Then one SDI TABLET was added to the resulting composition and allowed to thoroughly disperse.

TABLE I

| Ex. | Total Quat (ppm)[1] | Active Chlorine (ppm) | TB TEST 1 | TB TEST 2 | TB TEST 3 |
| --- | --- | --- | --- | --- | --- |
| 1A | 2640 | 0 | — | Fail | — |
| 1B | 5280 | 0 | — | Fail | — |
| 2A | 0 | 1100 | — | Fail | — |
| 2B | 0 | 2200 | — | Fail | — |
| 3 | 0 | 5106.2 | — | — | Pass |
| 4 | 0 | 5106.2 | — | — | Pass |
| 5A | 660 | 69 | Fail | — | — |
| 5B | 660 | 138 | Fail | — | — |
| 5C | 660 | 275 | Fail | — | — |
| 5D | 660 | 1100 | — | Pass | — |
| 5E | 660 | 2200 | — | Pass | — |
| 6A | 0 | 69 | Fail | — | — |
| 6B | 0 | 138 | Fail | — | — |
| 6C | 0 | 275 | Fail | — | — |

[1]Total amount of quaternary ammonium compound present.

Comparative Examples 1A and 1B tested the use of relatively high levels of quaternary ammonium compound in a disinfectant cleaner formulation, but no chlorine compound was added. These compositions were not effective against tubercule bacilli according to TB TEST 1.

Comparative Examples 2A and 2B show that the addition of 1100 ppm and 2200 ppm of bleach compound to a cleaner formulation was insufficient to make the composition tuberculocidal according to TB TEST 1.

Comparative Examples 3 and 4 verify literature reports that a level of about 5000 ppm of active chlorine level from bleach compounds such as sodium hypochlorite and sodium dichloroisocyanate produces disinfectant compositions that are tuberculocidal.

The results for Example 4 are somewhat contrary to the results for sodium hypochlorite reported in the Best et al. journal article noted above where an active chlorine level of 10,000 ppm was found to be necessary to pass the tuberculocidal activity test.

Examples 5A–5E show the result of increasing the amount of bleach compound, sodium dichlorisocyanate, present in a disinfectant composition relying on quaternary ammonium compounds for their disinfectant action. The quaternary ammonium compound level was kept essentially constant as more and more bleach compound was added. A synergistic effect between the quaternary ammonium compounds and the bleach compound was observed at active chlorine levels of 1100 and 2200 ppm according to TB TEST 1 since these compositions were unexpectedly found to be tuberculocidal. No such tuberculocidal effect was observed for Examples 1A and 1B even though much higher levels of the same quaternary ammonium compounds were present in the compositions tested. Likewise, Examples 2A and 2B showed that sodium dichloroisocyanate itself was not tuberculocidal the same levels of active chlorine as found in Examples 5D and 5E. Example 3 with more than twice the level of sodium dichloroisocyanate than Example 2B was found to be tuberculocidal in the absence of quaternary ammonium compounds.

Comparative Examples 6A–6C demonstrate that low amounts of bleach compound in another cleaner formulation did not possess tuberculocidal properties according to TB TEST 1.

EXAMPLES 7–12

These Examples provide further comparative and application examples of compositions employing different amounts of quaternary ammonium compounds and bleach compounds.

Comparative Example 7A was prepared by mixing 100 ml of 1:128 CONC. D with 100 ml of 1:20 LAUNDRY BLEACH.

Comparative Example 7B was prepared by mixing 100 ml of 1:128 CONC. D with 100 ml of 1:35 LAUNDRY BLEACH.

Comparative Example 7C was prepared by mixing 100 ml of 1:128 CONC. D with 100 ml of 1:45 LAUNDRY BLEACH.

Comparative Example 8A was prepared by mixing 100 ml of 1:256 CONC. D with 100 ml of 1:10 LAUNDRY BLEACH.

Comparative Example 8B was prepared by mixing 100 ml of 1:256 CONC. D with 100 ml of 1:20 LAUNDRY BLEACH.

Comparative Example 8C was prepared by mixing 100 ml of 1:256 CONC. D with 100 ml of 1:35 LAUNDRY BLEACH.

Comparative Example 9A was prepared by first dissolving four SDI TABLETS in 1890 ml of sterile purified water. Then 100 ml of that solution was mixed with 100 ml of 1:128 CONC. D.

Comparative Example 9B was prepared by first dissolving two SDI TABLETS in 1890 ml of sterile purified water. Then 100 ml of that solution was mixed with 100 ml of 1:128 CONC. D.

Application Example 10 was prepared by mixing 100 ml of 1:100 CONC. E with 100 ml of 1:20 LAUNDRY BLEACH.

Comparative Example 11 was prepared by first dissolving four SDI TABLETS in 1890 ml of sterile purified water. Then 100 ml of that solution was mixed with 100 ml of 1:10 CONC. F.

Comparative Example 12 was prepared by first dissolving four SDI TABLETS in 1890 ml of sterile purified water. Then 100 ml of that solution was mixed with 100 ml of CONC. G.

The active chlorine level in each of the resulting diluted disinfectant compositions was determined by the IODOMETRIC TITRATION METHOD within one hour of dilution. The pH of the compositions was also measured. These values are reported in Table II.

Table II also lists the calculated total levels of quaternary ammonium compounds for each diluted disinfectant composition having them. The results of evaluating the diluted disinfectant compositions by way of TB TEST 4 are reported in Table II.

TABLE II

| Ex. | Total Quat (ppm)[1] | Active Chlorine (ppm) | pH | TB TEST 4 |
|---|---|---|---|---|
| 7A | 660 | 975 | 9.1 | Fail |
| 7B | 660 | 532 | 9.06 | Fail |
| 7C | 660 | 434 | 9.08 | Fail |
| 8A | 330 | 2314 | 9.45 | Fail |
| 8B | 330 | 1285 | 9.08 | Fail |
| 8C | 330 | 479 | 9.05 | Fail |
| 9A | 660 | 940 | 6.14 | Fail |
| 9B | 660 | 434 | 6.29 | Fail |
| 10 | 800 | 1277 | 9.35 | Pass |
| 11 | 760 | 1196 | 8.94 | Fail |
| 12 | 2120 | 940 | 9.95 | Fail |

[1]Total amount of quaternary ammonium compound present.

Comparative Examples 7A–7C evaluated various levels of LAUNDRY BLEACH while keeping the total quaternary ammonium compound level at 660 ppm. None of these compositions passed TB TEST 4.

Comparative Examples 8A–8B evaluated the use of much higher levels of LAUNDRY BLEACH than in Examples 7A–7C, but used one-half of the total quaternary ammonium compound level. Neither disinfectant composition passed TB TEST 4.

Comparative Example 8C used about one-half of the amount of the total quaternary ammonium compound level and LAUNDRY BLEACH as in Comparative Example 7A. It failed to pass TB TEST 4.

Comparative Examples 9A and 9B were comparable to Examples 7A and 7C, respectively, except sodium dichloroisocyanate was used as the bleach compound. Both failed TB TEST 4.

Application Example 10 falls within the amount of total quaternary ammonium compound level and bleach compound (sodium hypochlorite) levels of the present invention. It passed TB TEST 4 and was thus considered to be a tuberculocidal disinfectant.

Comparative Example 11 gave an anomalous result which was not consistent with data obtained for similar compositions such as Example 5D, but was not retested. The composition was rated as passing TB TEST 4 until the very end of the test when it was considered to have failed. This may have been due to imprecisions in the test method or possible interference with disinfectant action by one of the other ingredients present in the cleaning composition.

Comparative Example 12 used a relatively high amount of total quaternary ammonium compound along with an amount of bleach compound below that found to be useful in the present invention. This composition failed TB TEST 4.

Based on the preceding Examples, a relatively narrow range of total quaternary ammonium compound (about 600 to 800 ppm) and active chlorine level from bleach compounds (about 1100 to 2500 ppm) gave synergistic compositions that were tuberculocidal disinfectant and cleaning compositions.

That which is claimed is:

1. A method of disinfecting a surface containing tubercule bacilli comprising applying to that surface a synergistic aqueous composition comprising, as disinfecting agents, an amount of a chlorine-containing bleach compound effective to provide from about 1,100 to about 2,500 parts per million by weight of available chlorine level and from about 600 to about 800 parts per million by weight of a bactericidal organic quaternary ammonium compound, wherein the bleach compound is selected from the group consisting of sodium hypochlorite, potassium hypchlorite, potassium dichloroisocyanurate and sodium dichloroisocyanurate and the quaternary ammonium compound is selected from the group consisting of di($C_8$–$C_{12}$ alkyl)dimethylammonium halides, ($C_{12}$–$C_{18}$ alkyl)dimethylbenzylammonium halides, ($C_{12}$–$C_{18}$ alkyl)dimethylethylbenzylammonium halides, and mixtures thereof.

2. The method of claim 1 wherein the quaternary ammonium compound is selected from the group consisting of di($C_8$–$C_{12}$ alkyl)dimethylammonium chlorides, ($C_{12}$–$C_{18}$ alkyl)dimethylbenzylammonium chlorides and mixtures thereof.

3. The method of claim 2 wherein the quaternary ammonium compound is selected from the group consisting of didecyldimethylammonium chloride, ($C_{12}$–$C_{16}$ alkyl)dimethylbenzylammonium chlorides and mixtures thereof.

4. The method of claim 3 wherein the composition contains an amount of bleach compound effective to provide from about 1,100 to 2,200 parts per million of available chlorine level and from about 650 to 700 parts per million of a mixture of didecyldimethylammonium chloride and ($C_{12}$–$C_{16}$ alkyl)dimethylbenzylammonium chlorides.

5. The method of claim 1 wherein the bleach compound is mixed with the quaternary ammonium compound just prior to the step of applying the composition to the surface.

6. A method of disinfecting a surface containing tubercule bacilli comprising applying to that surface a synergistic aqueous composition comprising, as disinfecting agents, an amount of sodium hypochlorite effective to provide from about 1,100 to about 2,500 parts per million by weight of available chlorine level and from about 600 to about 800 parts per million by weight of a mixture of didecyldimethylammonium chloride and ($C_{12}$–$C_{16}$ alkyl)dimethylbenzylammonium chlorides.

7. The method of claim 6 wherein the composition contains an amount of sodium hypochlorite effective to provide from about 1,100 to 2,200 parts per million of available chlorine level and from about 650 to 700 parts per million of a mixture of didecyldimethylammonium chloride and ($C_{12}$–$C_{16}$ alkyl)dimethylbenzylammonium chlorides.

8. The method of claim 6 wherein the sodium hypochlorite is mixed with the mixture of didecyldimethylammonium chloride and ($C_{12}$–$C_{16}$ alkyl)dimethylbenzylammonium chlorides just prior to the step of applying the composition to the surface.

9. The method of claim 6 wherein the mixture of didecyldimethylammonium chloride and ($C_{12}$–$C_{16}$ alkyl) dimethylbenzylammonium chlorides is in a ratio of 51.5:48.5 by weight.

10. A composition for disinfecting a surface containing tubercule bacilli comprising a synergistic aqueous composition comprising as, disinfecting agents, an amount of a chlorine-containino bleach compound effective to provide from about 1,100 to about 2,500 parts per million by weight of available chlorine level and from about 600 to about 800 parts per million by weight of a bactericidal organic quaternary ammonium compound, wherein the bleach compound is selected from the group consisting of sodium hypochlorite, potassium hypochlorite, potassium dichloroisocyanurate and sodium dichloroisocyanurate and the quaternary ammonium compound is selected from the group consisting of di($C_8$–$C_{12}$ alkyl)dimethylammonium halides, ($C_{12}$–$C_{18}$ alkyl)dimethylbenzylammonium halides and mixtures thereof.

11. The composition of claim 10 wherein the quaternary ammonium compound is selected from the group consisting of di($C_8$–$C_{12}$ alkyl)dimethylammonium chlorides, ($C_{12}$–$C_{18}$ alkyl)dimethylbenzylammonium chlorides and mixtures thereof.

12. The composition of claim 11 wherein the quaternary ammonium compound is selected from the group consisting of didecyldimethylammonium chloride, ($C_{12}$–$C_{16}$ alkyl) dimethylbenzylammonium chlorides and mixtures thereof.

13. The composition of claim 12 wherein the composition contains an amount of bleach compound effective to provide from about 1,100 to 2,200 parts per million of available chlorine level and from about 650 to 700 parts per million of a mixture of didecyldimethylammonium chloride and ($C_{12}$–$C_{16}$ alkyl)dimethylbenzylammonium chlorides.

14. A composition for disinfecting a surface containing tubercule bacilli comprising a synergistic aqueous composition comprising, as disinfecting agents, an amount of a chlorine-containing bleach compound effective to provide from about 1,100 to about 2,500 parts per million by weight of available chlorine level and from about 600 to about 800 parts per million by weight of a bactericidal organic quaternary ammonium compound wherein the bleach compound is maintained as a separate first component from the second component comprising the quaternary ammonium compound wherein the two components are mixed together just prior to application to the surface, wherein the bleach compound is selected from the group consisting of sodium hypochlorite, potassium hypochlorite, potassium dichloroisocyanurate and sodium dichloroisocyanurate and the quaternary ammonium compound is selected from the group consisting of di($C_8$–$C_{12}$ alkyl)dimethylammonium halides, ($C_{12}$–$C_{18}$ alkyl)dimethylbenzylammonium halides, ($C_{12}$–$C_{18}$ alkyl)dimethyl ethylbenzylammonium halides and mixtures thereof.

15. The composition of claim 14 wherein the quaternary ammonium compound is selected from the group consisting of di($C_8$–$C_{12}$ alkyl)dimethylammonium chlorides, ($C_{12}$–$C_{18}$ alkyl)dimethylbenzylammonium chlorides, and mixtures thereof.

16. The composition of claim 15 wherein the quaternary ammonium compound is selected from the group consisting of didecyldimethylammonium chloride, ($C_{12}$–$C_{16}$ alkyl) dimethylbenzylammonium chlorides, and mixtures thereof.

17. The composition of claim 16 wherein the composition contains an amount of bleach compound effective to provide from about 1,100 to 2,200 parts per million of available chlorine level and from about 650 to 700 parts per million of a mixture of didecyldimethylammonium chloride and ($C_{12}$–$C_{16}$ alkyl)dimethylbenzylammonium chlorides.

18. A composition for disinfecting a surface containing tubercule bacilli comprising a synergistic aqueous composition comprising, as disinfecting agents, an amount of sodium hypochlorite effective to provide from about 1,100 to about 2,500 parts per million by weight of available chlorine level and from about 600 to about 800 parts per million by weight of a mixture of didecyldimethylammonium chloride and ($C_{12}$–$C_{16}$ alkyl) dimethylbenzylammonium chlorides.

19. The composition of claim 18 wherein the composition contains an amount of sodium hypochlorite effective to provide from about 1,100 to 2,200 parts per million of available chlorine level and from about 650 to 700 parts per million of a mixture of didecyldimethylammonium chloride and ($C_{12}$–$C_{16}$ alkyl)dimethylbenzylammonium chlorides.

20. The composition of claim 18 wherein the mixture of didecyldimethylammonium chloride and ($C_{12}$–$C_{16}$ alkyl) dimethylbenzylammonium chlorides is in a ratio of 51.5:48.5 by weight.

* * * * *